US009040755B2

(12) United States Patent
Bajaj et al.

(10) Patent No.: US 9,040,755 B2
(45) Date of Patent: May 26, 2015

(54) HYDROGENATION OF STYRENE OXIDE FORMING 2-PHENYL ETHANOL

(71) Applicant: Council of Scientific and Industrial Research, New Delhi (IN)

(72) Inventors: Hari Chand Bajaj, Bhavnagar (IN); Sayed Hasan Razi Abdi, Bhavnagar (IN); Rukhsana Ilyas Kureshy, Bhavnagar (IN); Noor-Ul Hasan Khan, Bhavnagar (IN); Aasif Asharafbhai Dabbawala, Bhavnagar (IN); Tamal Roy, Bhavnagar (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 14/365,592

(22) PCT Filed: Dec. 14, 2012

(86) PCT No.: PCT/IN2012/000820
§ 371 (c)(1),
(2) Date: Jun. 13, 2014

(87) PCT Pub. No.: WO2013/088454
PCT Pub. Date: Jun. 20, 2013

(65) Prior Publication Data
US 2014/0330047 A1   Nov. 6, 2014

(30) Foreign Application Priority Data
Dec. 15, 2011   (IN) .......................... 3656/DEL/2011

(51) Int. Cl.
*C07C 29/132* (2006.01)
*B01J 23/44* (2006.01)
*B01J 23/58* (2006.01)
*B01J 27/236* (2006.01)
*B01J 29/74* (2006.01)
*B01J 35/00* (2006.01)
*B01J 35/10* (2006.01)
*B01J 37/00* (2006.01)
*B01J 37/02* (2006.01)

(52) U.S. Cl.
CPC ............... *C07C 29/132* (2013.01); *B01J 23/44* (2013.01); *B01J 23/58* (2013.01); *B01J 27/236* (2013.01); *B01J 29/7415* (2013.01); *B01J 35/002* (2013.01); *B01J 35/1014* (2013.01); *B01J 37/009* (2013.01); *B01J 37/0201* (2013.01); *B01J 2229/186* (2013.01)

(58) Field of Classification Search
None
See application file for complete search history.

(56) References Cited

U.S. PATENT DOCUMENTS

| 2,524,096 A | 10/1950 | Wood et al. |
| 2,822,403 A | 2/1958 | Hopff et al. |
| 3,579,593 A | 5/1971 | Wood |
| 4,064,186 A | 12/1977 | Gibson et al. |
| 4,943,667 A | 7/1990 | Hoelderich et al. |
| 6,166,269 A * | 12/2000 | Chaudhari et al. ............ 568/814 |

FOREIGN PATENT DOCUMENTS

| CA | 512236 A | 4/1955 |
| GB | 678589 A | 9/1952 |
| GB | 760768 A | 11/1956 |
| WO | WO-2013/088454 A1 | 6/2013 |

OTHER PUBLICATIONS

"Eurpoean Application Serial No. 12813994.6, Office Action mailed Aug. 28, 2014", 2 pgs.
"International Application No. PCT/IN2012/000820, Demand and Statement filed Oct. 7, 2013 in response to the International Search Report and Written Opinion mailed May 8, 2013", 8 pgs.
"International Application No. PCT/IN2012/000820, International Preliminary Report on Patentability dated Feb. 24, 2014", 7 pgs.
"International Application No. PCT/IN2012/000820, International Search Report mailed May 8, 2013", 5 pgs.
"International Application No. PCT/IN2012/000820, Written Opinion mailed May 8, 2013", 7 pgs.
Bergada, Olga, et al., "Effective catalysts, prepared from several hydrotalcites aged with and without microwaves, for the clean obtention of 2-phenylethanol", *Applied Catalysis A: General*, 331, (2007), 19-25.
Bergada, Olga, et al., "High-selective Ni-MgO catalysts for a clean obtention of 2-phenylethanol", *Applied Catalysis A: General*, 272(1-2), (2004), 125-132.
Bonini, Carlo, et al., "Oxirane Rings: Studies and Applications of a New Chemo and Regio Selective Reductive Opening of Epoxides", *Tetrahedron*, 45(10), (1989), 2895-2904.

(Continued)

*Primary Examiner* — Brian J Davis
(74) *Attorney, Agent, or Firm* — Schwegman Lundberg & Woessner, P.A.

(57) ABSTRACT

A process for preparation of 2-phenyl ethanol by catalytic hydrogenation of styrene oxide using a catalyst consisting of Pd (II) on basic inorganic support is investigated. The present invention comprises development of new Pd based catalysts. The present method yields 2-phenyl ethanol in 98% selectivity at total conversion of styrene oxide. The present process represents an environment friendly alternative to conventionally used methods in industry and eliminates the reduction step for catalyst preparation. In the present invention the active catalyst is generated in situ during the hydrogenation of styrene oxide. In addition, Pd (II) supported catalysts do not catch fire (non pyrophoric), can be stored under ambient conditions and produce very less or no dust which makes said catalysts suitable for industrial application.

11 Claims, 1 Drawing Sheet

(56) References Cited

OTHER PUBLICATIONS

Fujitsu, Hiroshi, et al., "Catalytic Hydrogenation of Styrene Oxide with Cationic Rhodium Complexes", *J. Org. Chem.*, 46(11), (1981), 2287-2290.

Kirm, I., et al., "Preparation of 2-phenylethanol by catalytic selective hydrogenation of styrene oxide using palladium catalysts", *Journal of Molecular Catalysis A: Chemical*, 239(1-2), (2005), 215-221.

Krishnamurthy, S., et al., "Lithium Triethylborohydride as a Convenient Reagent for the Facile Reduction of Both Hindered and Bicyclic Epoxides Prone to Electrophilically Induced Rearrangement", *Journal of the American Chemical Society*, 95(25), (1973), 8486-8487.

Kwon, Min Serk, et al., "Magnetically Separable Pd Catalyst for Highly Selective Epoxide Hydrogenolysis under Mild Conditions", *Org. Lett.*, 9(17), (2007), 3417-3419.

Mitsui, S., et al., "The deoxygenation in the catalytic hydrogenolysis of styrene oxides", *Tetrahedron*, 29(24), (1973), 4093-4097.

Noujima, Akifumi, et al., "Gold Nanoparticle-Catalyzed Environmentally Benign Deoxygenation of Epoxides to Alkenes", *Molecules*, 16(10), (2011), 8209-8227.

Ranu, Brindaban C., "Regio- and Stereo-selective Reductive Cleavage of Epoxides with Zinc Borohydride Supported on Silica Gel". *J. Chem. Soc., Chem. Commun.*, (1990), 1334-1335.

Rode, C. V., et al., "Reaction kinetics of the selective liquid phase hydrogenation of styrene oxide to beta-phenethyl alcohol", *Journal of Molecular Catalysis A: Chemical* 200(1-2), (2003), 279-290.

Smith, Janice G., "Synthetically Useful Reactions of Epoxides", *Synthesis*, 8, (1984), 629-656.

Smith, William B., "Ring Opening of Epoxides with Morpholine-Borane", *J. Org. Chem.*, 49(17), (1984), 3219-3220.

Sreekumar, R., et al., "Regioselective Reduction of Epoxides and Conjugated Carbonyl Compounds Using Zeolite Supported Zinc Borohydride", *Tetrahedron Letters*, 39(29), (1998), 5151-5154.

Yadav, Vasanti G., et al., "Synthesis of Phenethyl Alcohol by Catalytic Hydrogenation of Styrene Oxide", *Organic Process Research & Development*, 2(5), (1998), 294-297.

Yamada, Masafumi, et al., "Selective Reduction of Organic Compounds with Indium Hydride Reagents", *Tetrahedron Letters*, 36(18), (1995), 3169-3172.

\* cited by examiner

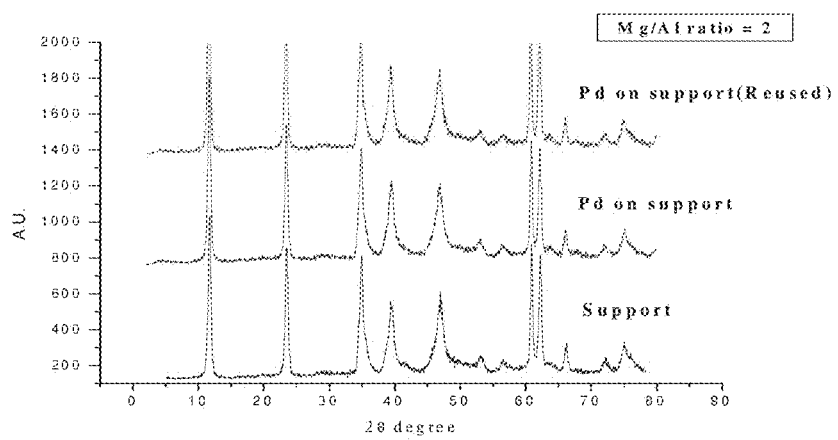
Fig. 1 XRD patterns for the support and catalyst
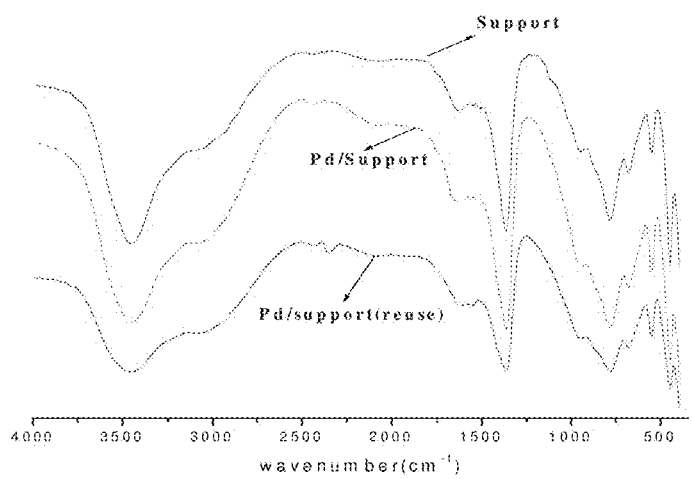
Fig. 2 FTIR spectra of the support and catalysts.

HYDROGENATION OF STYRENE OXIDE FORMING 2-PHENYL ETHANOL

PRIORITY CLAIM TO RELATED APPLICATIONS

This application is a U.S. national stage application filed under 35 U.S.C. §371 from International Application Serial No. PCT/IN2012/000820, which was filed Dec. 14, 2012, and published as WO 2013/088454 on Jun. 20, 2013, and which claims priority to Indian Application No. 3656/DEL/2011, filed Dec. 15, 2011, which applications and publication are incorporated by reference as if reproduced herein and made a part hereof in their entirety, and the benefit of priority of each of which is claimed herein.

FIELD OF THE INVENTION

The present invention relates to a process for the preparation of 2-phenyl ethanol by the hydrogenation of styrene oxide using Pd(II) salt on basic support precatalyst where the active catalyst Pd(0) generates in situ. More particularly, this invention relates to the preparation of highly efficient heterogeneous catalyst comprised of palladium on basic inorganic supports for the hydrogenation of styrene oxide to produce selectively 2-phenyl ethanol which is an important chemical for perfumery and pharmaceutical industries.

BACKGROUND OF THE INVENTION 2-phenylethanol (2-PEA) is the main component of the rose oils obtained from rose blossoms. 2-phenylethanol is a colorless liquid possessing a faint but lasting odor of rose petals, making it as a valuable chemical of commerce. 2-PEA is extensively used in perfumery, soaps and detergents, deodorant formulations and as food additive [B. D. Mookherjee, R. A. Wilson, Kirk-Othmer Encyclopedia of Chemical Technology, $4^{th}$ ed., vol. 17, John Wiley & Sons, New York, 1994]. 2-PEA has also bacteriostatic and antifungicidal properties and is frequently used in the formulations of cosmetics. Besides its direct application 2-PEA is also used as an intermediate in the synthesis of industrially important perfumery chemical compounds like synthetic Kewra (2-phenylethyl methyl ether). Due to the commercial importance of 2-phenyl ethanol various methods have been reported for its production.

Friedel-Crafts alkylation of benzene using ethylene oxide and stoichiometric quantities of aluminum chloride as catalyst has been used to produce 2-PEA on commercial scale [K. Bauer, D. Garbe, H. Surburg in Common Fragrance and Flavour Materials, New York, (1990), G. A. Olah, V. Prakash Reddy, G. K. Surya Prakash in Kirk-Othmer Encyclopedia of Chemical Technology, 4th ed., vol. 11, John Wiley & Sons, New York, (1994)]. Major disadvantages of this process are the fact that (i) Friedel-Crafts catalyst ($AlCl_3$) is corrosive hence requires the expansive corrosion resistance equipments, (ii) produces environmentally hazardous effluent in large quantities which causes effluent disposal problems and (iii) complete removal of the catalyst from the product is difficult.

2-phenylethanol is also prepared by the Grignard synthesis, starting from chlorobenzene, which is converted to phenyl-magnesium chloride, which then reacts with ethylene oxide to give phenylethoxy magnesium chloride. Phenylethoxy magnesium chloride thus obtained is decomposed with sulphuric acid to give 2-PEA. The main drawbacks of this process are (i) generation of potentially dangerous and air and moister sensitive phenyl-magnesium chloride (ii) requirement of sulphuric acid for the decomposition of Grignard complex and subsequent extraction of the desired product, (iii) produces large amounts of hazardous effluent and poor quality of the 2-phenylethanol which has low acceptability in perfumery industry [E. T. Theimer in Fragrance Chemistry, Academic Press, New York, (1982) p. 271].

The reductive cleavage of epoxides to alcohols is one of the most useful reactions in organic synthesis [H. Fujitsu, S. Shirahama, E. Matsumura, K. Takeshita, I. Mochida, J. Org. Chem. 46 (1981) 2287; S. Krishnamurthy, R. M. Schubert H. C. Brown, J. Am. Chem. Soc. 95 (1973) 8486]. In this process the required alcohol can be obtained by the ring opening of the corresponding epoxide using various hydrogenating agents [M. Bartok, K. L. Lang, in: A. Weissberger, E. C. Taylor (Eds.), The Chemistry of Heterocyclic Compounds-Small Ring Heterocycles, Wiley, New York, 1985] such as hydrides of alkaline metals like $LiAlH_4$, $LiAlH_4/AlCl_3$, $NaBH_4$, $B_2H_6$, $LiInH_4$, $LiPhInH_3$, $LiPhInH_2$, Borane/morpholine and zeolites/silica supported $Zn(BH_4)_2$ [M. Bartok, K. L. Lang, in: A. Weissberger, E. C. Taylor (Eds.), The Chemistry of Heterocyclic Compounds—Small Ring Heterocycles, Wiley, New York, 1985; G. Smith, Janice, Synthesis 8 (1984) 629; C. Bonini, R. D. Fabio, G. Sotgiu, S. Cavagnero, Tetrahedron 45 (1989) 2895-2904; M. Yamada, K. Tanaka, S. Araki, Y. Butsugan, Tetrahetdron Letters 36 (1995) 3169; W. B. Smith, J. Org. Chem. 49 (1984) 3219; R. Sreekumar, R. Padmakurmar, R. P. Rugmini, Tetrahedron Lett. 39 (1998) 5151; B. C. Ranu, A. R. Das, J. Chem. Soc. Chem. Commun. (1990) 1334]. The drawbacks of above stated methods are; (i) the product selectivity for the desired primary alcohol is poor, (ii) generates large of amount of salts which hampers effective separation of the product from the reaction mixture, (iii) All the above mentioned hydrogenating agents are expensive and (iv) potentially hazardous and need extra care for storage.

Several hydrogenation catalysts such as, Raney nickel, supported palladium and platinum catalysts have been reported to be good catalysts for the hydrogenation of styrene oxide [Wood, U.S. Pat. No. 2,524,096; Hopff et al., U.S. Pat. No. 2,822,403; U.S. Rubber Co., British Pat. Spec. No. 678, 589; Wood U.S. Pat. No. 3,579,593; Gibson et al., U.S. Pat. No. 4,064,186; Hoeldrich et al. U.S. Pat. No. 4,943,667; and Frisch, Canadian Pat. No. 512236. F Fujitsu, S. Shirahama, E. Matsumura, K. Takeshita, I. Mochida, J. Org. Chem. 46 (1981) 2287; C. V. Rode, M. M. Telkar, R. Jaganathan, R. V. Chaudhari, J. Mol. Catal A: Chem. 200 (2003) 279]. This reaction is also considered as most atom economical and environmentally benign method to produce 2-PEA. However, hydrogenation of styrene oxide is usually accompanied with formation of several side products such as phenyl acetaldehyde, 1-phenyl ethanol, styrene and ethyl benzene. These by-products when present in even a small amount may destroy the aroma of the 2-PEA, thus making it unsuitable for perfumery formulations.

Hopff et al. in U.S. Pat. No. 2,822,403, used a combination of Raney nickel and other hydrogenating catalyst like Cobalt, Platinum and Palladium for the catalytic hydrogenation of styrene oxide was then carried out in the presence of water and emulsifying agent to achieve high yield. However, this process has several disadvantages (i) need to remove large amount of water, (2) additional steps like solvent extraction, salting out process is necessary for product separation and (3) formation of ethyl benzene in large quantity.

A British Pat. No. 760768 describes the hydrogenation of styrene oxide with Raney nickel alone instead of combination of two catalysts using reaction conditions as given in preceding paragraph. This process suffers similar disadvantages as above.

Wood et al., in U.S. Pat. No. 3,579,593 described hydrogenation catalysts having varying content of Raney nickel and palladium in order to achieve high 2-PEA selectivity. However, to get higher 2-PEA selectivity (~96%) two stage temperature (stage 1. 30-40° C.; stage 2. 90-110° C.) and pressure (stage 1. ~50 psi; stage 2. ~200 psi) operation was required.

Recently, improved process for preparation of 2-PEA was also described in U.S. Pat. No. 6,166,269. This process produced 2-PEA with high selectivity via one step the catalytic hydrogenation of styrene oxide using platinum group metal catalysts supported on carbon/alumina in the presence of various organic/inorganic bases as promoter. However, the main disadvantages of this process are (i) requirement of organic and inorganic base promoters to increase 2-phenyl ethanol selectivity, (ii) removal of organic and inorganic base promoters after completion of reaction and (iii) requires large amounts of water to remove base promoters.

Several publications were dedicated on the use of Pd on carbon or Raney nickel as hydrogenation catalyst in presence or absence of a base promoter for the preparation of 2-PEA from styrene oxide. However, both these catalysts are highly pyrophoric, air sensitive and particularly nickel is toxic. [S. Mitsui, S. Imaizumi, M. Hisashige, Y. Sugi, Tetrahedron Lett. 29 (1973) 4093; V. G. Yadav, S. B. Chandalia, Org. Process Res. Dev. 2 (1998) 294; C. V. Rode, M. M. Telkar, R. Jaganathan, R. V. Chaudhari, J. Mol. Cat. A: Chemical 200 (2003) 279].

Olga Bergada et al. described the use of Ni supported on MgO [Appl. Catal. 272 (2004) 125] and hydrotalcite (Ni/Mg/Al) [Appl. Catal. 331 (2007) 19] for the hydrogenation of styrene oxide to give 2-PEA in high yield and selectivity. But a major drawback of these catalysts is that a strict air free condition is required to handle/store the catalyst. Further, to get the active catalyst the catalyst precursors were subjected to heating at very high temperature (350° C.) for 4 h with $H_2$ which is potentially hazardous.

Kirm et al. studied the gas phase hydrogenation of styrene oxide where vapors of hydrogen and styrene oxide in 20:1 molar ratio was passed over catalyst (Pd supported on activated carbon, MgO, $\gamma$-$Al_2O_3$) in a fixed bed reactor at temperature above 75° C. at a space velocity of 10,000-35,000 $h^{-1}$. They observed that high selectivity of 2-PEA was obtained in the case of basic support [J. Mol. Cat. A: Chemical 239 (2005) 215]. However, the drawbacks of above catalyst systems are; (i) the requirement of either special device for the reduction of Pd precursors using $H_2$ gas at 350° C. (ii) the catalyst thus prepared needed to store under air-free conditions (iii) need to use large excess of hydrogen.

The above discussed processes suffer from various obstacles such as use of hazardous/toxic reagents/catalysts, produces large amount of effluent, separation of the catalyst used, low selectivity of 2-PEA, requirement of basic promoters to enhance selectivity of 2-PEA, requirement of special device or chemical reagent for reduction of the metal precursors used, catalyst sensitivity, stability and catalyst recycling.

In view of this, we have developed a catalyst where Pd (II) was loaded on basic inorganic support. The supported Pd (II) catalysts thus prepared generate Pd (0) in situ to catalyze hydrogenation of epoxide substrate. Therefore, an additional step of metal reduction was avoided. Additionally Pd (II) catalysts are non-pyrophoric (do not catch fire in air) and sufficiently stable under ambient condition (no change in catalyst performance was observed over a period of six months when stored in a tightly closed bottle at room temperature whose temperature ranged varied over 20-35° C. under atmospheric condition that is to say, no artificially created inert atmosphere). Which makes the handling easier and do not require special care for their storage. Further, Pd (II) supported on basic inorganic supports are heavier than conventionally used Pd (0) on carbon, therefore produce no or little dust. Furthermore, the selectivity for the desired product is very high with as developed catalysts, which is consistent over many catalyst-reuse experiments. Due to these qualities, the Pd/basic inorganic support is suitable for large scale hydrogenation of styrene oxide as demonstrated in some of the examples given in the present patent and have significantly better alternative to the currently used catalyst in terms of economy, safety, and eco-friendly nature.

OBJECTIVES OF THE INVENTION

The main object of the present invention is to provide a process for the preparation of 2-phenyl ethanol by hydrogenation of styrene oxide using Pd(II) salt on basic support precatalyst where the active catalyst Pd(0) generates in situ which eliminates the drawbacks as detailed above.

Another object of the invention is to provide improved catalyst based on Pd having various advantages over currently used catalysts for the selective preparation of 2-Phenylethanol.

Yet another object of the present invention is to provide a process for the preparation of 2-phenyl ethanol using Pd (II) supported catalyst which eliminates the reduction step for catalyst preparation as active catalyst is generated in situ during hydrogenation reaction.

Yet another object of the present invention is to provide a process for the preparation of 2-phenyl ethanol using Pd supported catalysts which do not catch fire (non pyrophoric), can be stored under ambient condition for long (tested for 1 year) without any noticeable loss in its catalytic performance and produce very less or no dust.

Yet another object of the present invention is to provide a process for the preparation of 2-phenyl ethanol using a catalyst where Pd loaded on basic inorganic support which eliminates the additional use of basic promoters to increase selectivity of 2-phenyl ethanol.

Yet another object of the present invention is to provide a process for the selective production of 2-phenyl ethanol using Pd supported catalysts.

Still another object of the present invention is to provide a process for the preparation of 2-phenyl ethanol using a Pd supported catalyst which could be easily separated from the reaction mixture and effectively recycle.

SUMMARY OF THE INVENTION

Brief Description of Drawing

FIG. 1. XRD patterns for the support (lower most spectrum), Pd on support (middle spectrum) and Pd on support after first use (upper most spectrum) in the hydrogenation of styrene oxide. All the graphs show high crystallinity which do not change after catalytic use.

FIG. 2. FTIR spectra; of the samples in KBr pellet recorded on Perkin-Elmer GX-FTIR over the wavelength range of 4000 to 400 $cm^{-1}$ (lower most spectrum) support hydrotalcite, Pd on hydrotalcite and Pd on hydrotalcite (reused) show identical spectra suggesting no alteration in support during the loading of the Pd and after the use of the supported catalyst in the hydrogenation of styrene oxide.

DETAIL DESCRIPTION OF THE INVENTION

The present invention describes the improved process for preparation of 2-phenyl ethanol by catalytic hydrogenation of styrene oxide using a catalyst consisting of Pd(II) on basic inorganic support, which comprises development of new Pd based catalyst eliminates the reduction step for catalyst preparation as active catalyst is generated in situ during hydrogenation reaction. The developed Pd supported catalysts do not catch fire (non pyrophoric), can be stored under ambient conditions for long (tested for 1 year) without any noticeable loss in its catalytic performance and produce very less or no dust. The present method yields 98% selectivity to 2-phenyl ethanol at total conversion of styrene oxide under optimized condition.

In the following passages the preparation and characterization of Pd supported catalyst for the hydrogenation of styrene oxide is described.

1. Preparation of Catalyst a) To impregnate the Pd salt to basic inorganic support, an appropriate amount of Pd salt is placed together with solvent and support in a round bottom flask fitted with an efficient water condenser and refluxing the mixture for a period of 18 to 24 hours.

b) Filtration of reaction mixture from step a) and washing of the resultant solid catalyst with a suitable solvent.

c) The solid (catalyst) is dried at 120° C. in an oven for 12 h.

Characterization of catalyst was done by various physicochemical technique like BET surface area, pore diameter, pore volume, Powder X-ray diffraction (XRD), Fourier transform infrared (FT-IR) spectra and Scanning electron microscopy: The metal contents in the catalysts were determined by inductively coupled plasma (ICP).

2. Catalytic Hydrogenation of Styrene Oxide to Produce 2-phenylethanol a) In a typical hydrogenation experiment, required amount of Palladium catalyst (with 0.01 to 10% Pd loading), substrate styrene oxide (sub:cat.=5-200 w/w), solvent (solvent/sub=1-10) were charged into a stainless steel autoclave 100 mL reactor.

b) The stirring rate was adjusted to 300-2000 rpm.

c) The reactor was then flushed thrice with hydrogen gas at room temperature (27° C. 3° C.) and then pressurized with hydrogen gas at a desired pressure (15-800 psi).

d) The pressurized reaction mixture was stirred at 300-2000 rpm at room temperature (27±3° C.). The hydrogen gas pressure inside the reactor was maintained at operating pressure by intermittent supply of hydrogen gas from cylinder. After there was no further drop in pressure, the stirring was stopped and the reactor was allowed to attain room temperature (27° C.±3° C.).

e) The reactor was depressurized, opened, and the supernatant was decanted from the reaction mixture leaving behind the settled catalyst inside the reactor, which was reused without purification for the next hydrogenation run.

f) The solvent is removed from the supernatant obtained from step (e) by distillation to get the final product.

The present invention relates to the preparation of 2-phenyl ethanol suitable for various applications. The inventive steps adopted in the presence invention are (i) the catalyst used in the reaction does not require before hand reduction of Pd(II) for the hydrogenation of styrene oxide, hence obviate the additional use of various reducing agents and associated special devices for the reduction of Pd(II) (ii) Pd(II) supported catalysts do not catch fire (non pyrophoric), can be stored under ambient condition (tested for 1 year) and produce very less or no dust. (iii) due to the use of a basic support for Pd, the use of additional basic promoters such as NaOH, KOH, $Na_2CO_3$, $K_2CO_3$, triethyl amine, diethyl amine and pyridine to increase selectivity of 2-phenyl ethanol is not required in the present invention (iv) Pd supported catalyst synthesized in the present invention is separated easily from the reaction mixture and effectively recycled.

The following examples are given by way of illustration of the present invention and therefore should not be construed to limit the scope of the present invention.

EXAMPLE 1

Pd-2-HT

To impregnate the Pd salt on Hydrotalcite (HT), 66.4 mg of $PdCl_2$ salt, 50 mL ethanol and 2.0 g of hydrotalcite support (Mg/Al=2) were charged in a 2-necked 150 mL round bottom flask equipped with a mechanical stirrer and a reflux condenser connected to a nitrogen inlet. The resulting mixture was stirred at reflux temperature (78° C.) under an $N_2$ atmosphere for a period of 20 hours. The reaction mixture is then filter to obtain solid material, followed by washing of the resultant solid catalyst with solvent. Finally, the solid (catalyst) is dried at 120° C. in an oven for 12 h.

Characterization of Catalyst a) BET surface areas, pore diameters, and pore volumes were calculated from nitrogen adsorption-desorption isotherms that were obtained at −196° C. using a Micromeritics ASAP 2010 instrument. Samples were outgassed in vacuo at 100° C. for 12 h prior to use. Specific surface areas were calculated by the BET method and pore distribution was established by the BJH method. Table-1 presents the surface areas of hydrotalcite before Pd impregnation (entry 1), after Pd impregnation (entry 2) and recovered Pd-impregnated catalyst after first cycle of hydrogenation of styrene oxide (entry 3). These entries clearly indicate the formation of Pd-impregnated hydrotalcite and demonstrate that the structure of the impregnated catalyst is intact after the styrene oxide hydrogenation react.

TABLE 1 surface areas of hydrotalcite before Pd impregnation and after Pd impregnation

| entry | Support/Catalyst | BET, Surface area m$^2$/g |
|---|---|---|
| 1 | HT | 70.5 |
| 2 | Pd on HT | 69.7 |
| 3 | Pd on HT (after 1$^{st}$ use) | 65.4 | b) X-ray diffraction (XRD) analysis was performed in order to check for crystallinity Powder X-ray diffraction (P-XRD) patterns of hydrotalcite samples were recorded with powder diffractometer (Philips, X'Pert MPD system) using Cu—Kα radiation (λ=1.54056 Å). Scans were performed over the 2θ range from 2 to 80°.

FIG. 1 shows the XRD patterns for the support (blue line), Pd on support (black line) and Pd on support after first use (reused) in the hydrogenation of styrene oxide. All the graphs show high crystallinity which do not change after catalytic use.

c) Fourier transform infrared (FT-IR) spectra of the samples were recorded with Perkin-Elmer GX-FTIR system using KBr pellet in the wavelength range of 4000 to 400 cm$^{-1}$ with a resolution of 4 cm$^{-1}$. The FTIR spectrum for the support, Pd on support and Pd on support (reused) show identical spectra suggesting no alteration in support during the loading of the Pd and after the use of the supported catalyst in the hydrogenation of styrene oxide. (FIG. 2)

d) The metal content in the catalyst was determined by ICP (Perkin-Elmer ICP-OES instrument) under standard conditions. The Pd content in the catalyst was found to be 1.98% w/w.

EXAMPLE 2

Pd-2-MgO

To impregnate the Pd salt on MgO, 66.4 mg of PdCl$_2$ salt, 50 mL ethanol and MgO (2.0 g) were charged in a 2-necked 150 mL round bottom flask equipped with a mechanical stirrer and a reflux condenser connected to a nitrogen inlet. The resulting mixture was stirred at reflux temperature (78° C.)) under an N$_2$ atmosphere for a period of 20 hours. The reaction mixture is then filter to obtain solid material, followed by washing of the resultant solid catalyst with solvent. Finally, the solid (catalyst) is dried at 120° C. in oven for 12 h. The Pd content in the catalyst were determined by ICP (Perkin-Elmer ICP-OES instrument) under standard conditions. The Pd content in the catalyst was found to be 1.96% w/w.

EXAMPLE 3

Pd-2-CaO

To impregnate the Pd salt on CaO, 66.4 mg of PdCl$_2$ salt, 50 mL ethanol and CaO (2.0 g) were charged in a 2-necked 150 mL round bottom flask equipped with a mechanical stirrer and a reflux condenser connected to a nitrogen inlet. The resulting mixture was stirred at reflux temperature (78° C.) under an N$_2$ atmosphere for a period of 20 hours. The reaction mixture is then filter to obtain solid material, followed by washing of the resultant solid catalyst with solvent. Finally, the solid (catalyst) is dried at 120° C. in oven for 12 h. The Pd content in the catalyst were determined by ICP (Perkin-Elmer ICP-OES instrument) under standard conditions. The Pd content in the catalyst was found to be 1.93% w/w.

EXAMPLE 4

Pd-2-Alumina

To impregnate the Pd salt on alumina, 66.4 mg of PdCl$_2$ salt, 50 mL ethanol and alumina (2.0 g) were charged in a 2-necked 150 mL round bottom flask equipped with a mechanical stirrer and a reflux condenser connected to a nitrogen inlet. The resulting mixture was stirred at reflux temperature (78° C.) under an N$_2$ atmosphere for a period of 20 hours. The reaction mixture is then filter to obtain solid, material, followed by washing of the resultant solid catalyst with solvent. Finally, the solid (catalyst) is dried at 120° C. in oven for 12 h. The Pd content in the catalyst were determined by ICP (Perkin-Elmer ICP-OES instrument) under standard conditions. The Pd content in the catalyst was found to be 1.98% w/w.

EXAMPLE 5

Pd-2-Barium Carbonate

To impregnate the Pd salt on barium carbonate, 66.4 mg of PdCl$_2$ salt, 50 mL ethanol and barium carbonate (2.0 g) were charged in a 2-necked 150 mL round bottom flask equipped with a mechanical stirrer and a reflux condenser connected to a nitrogen inlet. The resulting mixture was stirred at reflux temperature (78° C.) under an N$_2$ atmosphere for a period of 20 hours. The reaction mixture is then filter to obtain solid material, followed by washing of the resultant solid catalyst with solvent. Finally, the solid (catalyst) is dried at 120° C. in oven for 12 h. The Pd content in the catalyst were determined by ICP (Perkin-Elmer ICP-OES instrument) under standard conditions. The Pd content in the catalyst was found to be 1.92% w/w.

EXAMPLE 6

Pd-2-Calcium Carbonate

To impregnate the Pd salt on calcium carbonate, 66.4 mg of PdCl$_2$ salt, 50 mL ethanol and calcium carbonate (2.0 g) were charged in a 2-necked 150 mL round bottom flask equipped with a mechanical stirrer and a reflux condenser connected to a nitrogen inlet. The resulting mixture was stirred at reflux temperature (78° C.) under an N$_2$ atmosphere for a period of 20 hours. The reaction mixture is then filter to obtain solid material, followed by washing of the resultant solid catalyst with solvent. Finally, the solid (catalyst) is dried at 120° C. in oven for 12 h. The Pd content in the catalyst were determined by ICP (Perkin-Elmer ICP-OES instrument) under standard conditions. The Pd content in the catalyst was found to be 1.91% w/w.

EXAMPLE 7

Pd-2-Na Beta Zeolite

To impregnate the Pd salt on Na beta zeolite (commercial grade), 66.4 mg of PdCl$_2$ salt, 50 mL ethanol and Na beta zeolite (2.0 g) were charged in a 2-necked 150 mL round bottom flask equipped with a mechanical stirrer and a reflux condenser connected to a nitrogen inlet. The resulting mixture was stirred at reflux temperature (78° C.) under an N$_2$ atmosphere for a period of 20 hours. The reaction mixture is then filter to obtain solid material, followed by washing of the resultant solid catalyst with solvent. Finally, the solid (catalyst) is dried at 120° C. in oven for 12 h. The Pd content in the catalyst were determined by ICP (Perkin-Elmer ICP-OES instrument) under standard conditions. The Pd content in the catalyst was found to be 1.95% w/w.

EXAMPLE 8

Pd-1-HT

To impregnate the Pd salt on Hydrotalcite (HT), 33.2 mg of PdCl$_2$ salt, 50 mL ethanol and 2.0 g of hydrotalcite support (Mg/Al=2) were charged in a 2-necked 150 mL round bottom flask equipped with a mechanical stirrer and a reflux condenser connected to a nitrogen inlet. The resulting mixture was stirred at reflux temperature 78° C. under an N$_2$ atmosphere for a period of 20 hours. The reaction mixture is then filter to obtain solid material, followed by washing of the resultant solid catalyst with solvent. Finally, the solid (catalyst) is dried at 120° C. in oven for 12 h. The Pd content in the catalyst was determined by ICP (Perkin-Elmer ICP-OES instrument) under standard conditions. The Pd content in the catalyst was found to be 0.96% w/w.

EXAMPLE 9

Pd-3-HT

To impregnate the Pd salt on Hydrotalcite (HT), 99.6 mg of $PdCl_2$ salt, 50 mL ethanol and 2.0 g of hydrotalcite support (Mg/Al=2) were charged in a 2-necked 150 mL round bottom flask equipped with a mechanical stirrer and a reflux condenser connected to a nitrogen inlet. The resulting mixture was stirred at reflux temperature (78° C.) under an $N_2$ atmosphere for a period of 20 hours. The reaction mixture is then filter to obtain solid material, followed by washing of the resultant solid catalyst with solvent. Finally, the solid (catalyst) is dried at 120° C. in oven for 12 h. The Pd content in the catalyst was determined by ICP (Perkin-Elmer ICP-OES instrument) under standard conditions. The Pd content in the catalyst was found to be 2.92% w/w.

EXAMPLE 10

Pd-5-HT

To impregnate the Pd salt on Hydrotalcite, 166 mg of $PdCl_2$ salt, 50 mL ethanol and 2.0 g of hydrotalcite support (Mg/Al=2) were charged in a 2-necked 150 mL round bottom flask equipped with a mechanical stirrer and a reflux condenser connected to a nitrogen inlet. The resulting mixture was stirred at reflux temperature (78° C.) under an $N_2$ atmosphere for a period of 20 hours. The reaction mixture is then filter to obtain solid material, followed by washing of the resultant solid catalyst with solvent. Finally, the solid (catalyst) is dried at 120° C. in oven for 12 h. The Pd content in the catalyst were determined by ICP (PerkinElmer ICP-OES instrument) under standard conditions. The Pd content in the catalyst was found to be 4.90% w/w.

EXAMPLE 11 TO 16

These examples demonstrate the effect of basic support in the Pd catalyzed hydrogenation of styrene oxide to 2-phenyl ethanol.

Styrene oxide (5 g; 41.67 mmol), methanol (50 mL) and Catalyst (100 mg) were charged in a 100 mL stainless steel autoclave equipped with magnetic drive agitator. The reactor was flushed thrice with hydrogen gas at room temperature (27±3° C.) and then pressurized with hydrogen gas at 500 psig. The reaction mass was stirred at a speed of 1200 rpm at room temperature (78° C.) for a period 3 hours. The hydrogen gas pressure inside the reactor was maintained at 500 psig by intermittent supply of hydrogen gas from cylinder through out the reaction period. After reaction, the reactor depressurized, opened and the content of the reactor was allowed to filter through whatman filter paper No. 4. The filtrate was subjected to GC analysis that showed complete conversion of styrene oxide with 98.5% selectivity for 2-phenyl ethanol. The other 2% constituted 2-phenyl acetaldehyde (major), 2-methoxy ethyl benzene (minor) and 1,2 dimethoxy ethyl benzene (trace). The residue was washed with methanol (2×5 mL) and used as catalyst for the fresh run of styrene oxide hydrogenation. Table 2 presents the results for the hydrogenation of styrene oxide with commercially available Pd—S—C (Pd on carbon, 5%) (example 11) and Pd—S—C (Pd on carbon, 5%) in the presence of NaOH (100 mg) as an additive (example 12). The results of as synthesized catalysts are given in Table 2 (examples 13-16).

TABLE 2

| Example | Catalyst | Pd Loading (% w/w) | Conv. (%) | $S_{2-PEA}$ (%) |
|---|---|---|---|---|
| 11 | Pd-5-C | 5 | 100 | 84 |
| 12[b] | Pd-5-C | 5 | 100 | 98 |
| 13 | Pd-5-HT (Mg/Al = 2.0) | 5 | 100 | 98 |
| 14 | Pd-5-HT (Mg/Al = 3.0) | 5 | 100 | 98.5 |
| 15 | Pd-5-MgO | 5 | 100 | 98 |
| 16 | Pd-5-basic alumina | 5 | 100 | 98 |

Reaction conditions: Styrene oxide = 5 g; 41.67 mmol, Catalyst = 100 mg, Temp. = 30° C., Press. = 500 psig, Solvent (Methanol) = 50 mL time, 3 h.
[b]NaOH = 100 mg

EXAMPLE 15 TO 25

These examples demonstrate the effect of temperature, hydrogen gas pressure, Pd loading (examples 15 to 20) and catalyst recycle test (examples 21 to 25) in the Pd/Hydrotalcite catalyzed hydrogenation of styrene oxide to 2-phenyl ethanol.

Styrene oxide (5 g; 41.67 mmol), methanol (50 mL) and Pd-5-Hydrotalcite (100 mg) were charged in a 100 mL stainless steel autoclave equipped with magnetic drive agitator. The reactor was flushed thrice with hydrogen gas at room temperature (27±3° C.) and then pressurized with required hydrogen gas pressure. The reaction mass was stirred at speed of 1200 rpm at (27±3° C.) for 3 hours. The reaction started immediately as was evidenced by a pressure drop with increase in the temperature. The hydrogen gas pressure inside the reactor was maintained by intermittent supply of hydrogen gas from cylinder through out the reaction period. After the reaction was completed, the reactor was cooled, depressurized, opened and the content of the reactor was allowed to filter through whatman filter paper No. 4. The filtrate was subjected to GC analysis. The residue was washed with methanol (2×5 mL) and used as catalyst for the fresh run of styrene oxide hydrogenation.

Table 3 presents the effect of temperature, hydrogen gas pressure, and Pd loading (examples 15 to 20) on conversion and selectivity in Pd catalyzed hydrogenation of styrene oxide. Moreover, supported Pd catalyst can effectively recycle without significant lose in catalytic activity and selectivity (examples 21 to 25).

TABLE 3

| Example | Catalyst | Pd loading (% w/w) | Temp. (° C.) | Press. (psig) | Conv. (%) | $S_{2-PEA}$ (%) |
|---|---|---|---|---|---|---|
| 15 | Pd-5-HT | 5 | 50 | 500 | 100 | 97 |
| 16 | Pd-5-HT | 5 | 30 | 145 | 100 | 98 |
| 17 | Pd-5-HT | 5 | 30 | 290 | 100 | 98 |
| 18 | Pd-1-HT | 1 | 30 | 500 | 100 | 96 |
| 19 | Pd-3-HT | 3 | 30 | 500 | 100 | 97 |
| 20 | Pd-0.5-HT | 0.5 | 30 | 500 | 100 | 90 |
| 21 | Pd-5-HT | 5 | 30 | 290 | 100 | 98 |
| 22 | $I^{st}$ recycle | 5 | 30 | 290 | 100 | 98 |
| 23 | $II^{nd}$ recycle | 5 | 30 | 290 | 100 | 98 |
| 24 | $III^{rd}$ recycle | 5 | 30 | 290 | 100 | 97 |
| 25 | $IV^{th}$ recycle | 5 | 30 | 290 | 100 | 98 |

Reaction conditions: Styrene oxide = 5 g; 41.67 mmol, Catalyst = 100 mg, Solvent (Methanol) = 50 mL, time 3 h.

The main advantages of the present invention are:
1. The catalytic hydrogenation of styrene oxide is feasible with direct use Pd(II) supported catalyst, without prior reduction of Pd(II) to Pd(0).
2. Pd(II) supported catalyst is easy to synthesized which is non pyrophoric, can be stored in air for long (tested for over 1 year) without any noticeable loss in its catalytic performance.

3. The as synthesized catalyst produce very less or no dust as in the case of conventionally used Pd on carbon.

4. The as synthesized catalysts do not require a basic promoter to increase selectivity of 2-phenyl ethanol.

5. The as synthesized catalysts can be directly reused after the first cycle of hydrogenation of styrene oxide by simple decantation of the product from liquid phase without involving any purification/filtration step.

6. The present method yields 2-phenyl ethanol with 98.5% selectivity at total conversion of styrene oxide.

7. The catalyst can be effectively recycled many cycles (tested for 25 cycles) without any significant loss in activity and selectivity.

We claim:

1. A process for the preparation of 2-phenyl ethanol using Pd(II) salt on a basic support as precatalyst without calcination, wherein said process comprises the steps of:
   (a) mixing styrene oxide, an organic solvent and Pd(II) salt on basic support as precatalyst under stirring followed by flushing the reaction mixture with hydrogen gas at a temperature ranging between 24° C. to 30° C.;
   (b) pressurizing the reaction mixture as obtained in step (a) with hydrogen gas at 400-800 pounds per square inch gauge (psig) followed by stirring at a speed rate ranging between 800-1300 revolutions per minute (rpm) at a temperature ranging between 24° C. to 30° C. for a period ranging between 1 h to 5 h, subsequently maintaining hydrogen pressure inside the reactor by intermittent supply of hydrogen gas;
   (c) depressurizing the reaction mixture as obtained in step (b) at a temperature ranging between 24° C. to 30° C.;
   (d) separating the catalyst Pd(0) on a basic support which generates in situ from the reaction mixture as obtained in step (c) by decantation/filtration and obtaining 2-phenyl ethanol with organic solvent; and
   (e) distilling the solvent from 2-phenyl ethanol with organic solvent as obtained in step (d) to obtain solid 2-phenyl ethanol.

2. The process as claimed in claim 1, wherein the Pd (II) salt in step (a) is selected from the group consisting of chloride, bromide, iodide, nitrate, oxide, cyanide, sulfate, trifluoroacetate, acetate, acetylacetonate and tetraammine dichloro.

3. The process as claimed in claim 1, wherein the basic support in step (a) is selected from the group consisting of hydrotalcite, MgO, CaO, basic alumina, barium carbonate, calcium carbonate, and alkali zeolites.

4. The process as claimed in claim 3, wherein hydrotalcite is used having Mg: Al ratio ranging from 2 to 6 by weight.

5. The process as claimed in claim 1, wherein the loading of Pd on the basic support in step (a) is in the range of 0.1 to 10% by weight.

6. The process as claimed in claim 1, wherein loading of Pd on the basic support in step (a) is carried out by an impregnation method.

7. The process as claimed in claim 1, wherein Pd(II) on a basic support in step (a) is used with styrene oxide: precatalyst ratio ranging from 5 to 200 by weight.

8. The process as claimed in claim 1, wherein the organic solvent used in step (a) is selected from methanol, ethanol, propanol, isopropanol, butanol, 1,4-dioxane, tetrahydrofuran, acetone, acetonitrile, toluene, benzene, cyclohexane, hexane, N,N-dimethylformamide, N,N-dimethylacetamide, chloroform, carbon tetrachloride, dichloromethane and dichloroethane.

9. The process claimed in claim 1, wherein selectivity of 2-phenyl ethanol is in the range of 90-99%.

10. The process as claimed in claim 3, wherein the zeolite is Na beta zeolite or Na ZSM-5.

11. A process for the preparation of 2-phenyl ethanol comprising:
   contacting styrene oxide, in an organic solvent, with Pd(0) catalyst generated in situ from Pd(II) precatalyst on a basic support without calcination to obtain 2-phenyl ethanol dissolved in the organic solvent;
   separating the Pd(0) catalyst on the basic support; and
   removing the solvent to obtain 2-phenyl ethanol.

* * * * *